(12) United States Patent
Liu et al.

(10) Patent No.: US 11,266,859 B2
(45) Date of Patent: Mar. 8, 2022

(54) NEUTRON CAPTURE THERAPY SYSTEM

(71) Applicant: NEUBORON MEDTECH LTD., Jiangsu (CN)

(72) Inventors: Yuan-hao Liu, Jiangsu (CN); Wei-Hua Lu, Jiangsu (CN)

(73) Assignee: NEUBORON MEDTECH LTD., Jiangsu (CN)

( * ) Notice: Subject to any disclaimer, the term of this patent is extended or adjusted under 35 U.S.C. 154(b) by 8 days.

(21) Appl. No.: 16/880,161

(22) Filed: May 21, 2020

(65) Prior Publication Data

US 2020/0282238 A1 Sep. 10, 2020

Related U.S. Application Data

(63) Continuation of application No. PCT/CN2018/100787, filed on Aug. 16, 2018.

(30) Foreign Application Priority Data

Dec. 15, 2017 (CN) .......................... 201711347618.5
Dec. 15, 2017 (CN) .......................... 201721763785.3

(51) Int. Cl.
*A61N 5/10* (2006.01)
*G21G 4/02* (2006.01)

(52) U.S. Cl.
CPC ............. *A61N 5/1077* (2013.01); *G21G 4/02* (2013.01); *A61N 2005/109* (2013.01);
(Continued)

(58) Field of Classification Search
CPC ............ A61N 5/1077; A61N 2005/109; A61N 2005/1094; A61N 2005/1095;
(Continued)

(56) References Cited

U.S. PATENT DOCUMENTS 5,174,949 A * 12/1992 Johansson .............. G21C 3/332
376/439
5,247,551 A * 9/1993 van Swam ............. G21C 3/336
376/441
(Continued)

FOREIGN PATENT DOCUMENTS

CN 101829409 A 9/2010
CN 105917251 A 8/2016
(Continued)

OTHER PUBLICATIONS

International Search Report of PCT/CN2018/100787, dated Oct. 29, 2018.

*Primary Examiner* — David A Vanore
(74) *Attorney, Agent, or Firm* — Locke Lord LLP; Tim Tingkang Xia, Esq.

(57) ABSTRACT

A neutron capture therapy system, including a beam shaping assembly and a vacuum tube. The beam shaping assembly includes a beam entrance, an accommodating cavity accommodating the vacuum tube, a moderator adjacent to an end of the accommodating cavity, a reflector surrounding the moderator, a radiation shield disposed in the beam shaping assembly, and a beam exit. A target is disposed at an end of the vacuum tube, nuclear reactions occur between the target and a charged particle beam entering through the beam entrance to generate neutrons. The moderator moderates the neutrons, the reflector guides deflected neutrons back to the moderator. The moderator at least includes two cylindrical moderating members with different outer diameters respectively, the moderator has a first end close to the beam entrance and a second end close to the beam exit, and the target is accommodated between the first end and the second end.

20 Claims, 6 Drawing Sheets

(52) U.S. Cl.
CPC ............... *A61N 2005/1094* (2013.01); *A61N 2005/1095* (2013.01); *A61N 2005/1098* (2013.01)

(58) Field of Classification Search
CPC .......... A61N 2005/1098; A61N 5/1042; A61N 5/10; G21G 4/02; G21F 3/00; H05H 6/00; H05H 3/06; G21K 1/00
See application file for complete search history.

(56) References Cited

U.S. PATENT DOCUMENTS

| | | | | |
|---|---|---|---|---|
| 5,267,286 A | * | 11/1993 | Hirukawa | G21C 7/113 376/353 |
| 6,301,321 B1 | * | 10/2001 | Farawila | G21C 3/322 376/444 |
| 10,744,345 B2 | * | 8/2020 | Liu | A61N 5/10 |
| 10,926,110 B2 | * | 2/2021 | Liu | A61N 5/1048 |
| 2010/0019164 A1 | * | 1/2010 | Stephan | G01T 3/00 250/390.04 |
| 2011/0090710 A1 | * | 4/2011 | Kelly | F24S 50/20 362/562 |
| 2011/0255651 A1 | * | 10/2011 | Bashkirtsev | G21C 5/20 376/412 |
| 2012/0027152 A1 | * | 2/2012 | Reese | G21G 1/00 376/190 |
| 2013/0129027 A1 | * | 5/2013 | Pantell | H05H 3/06 376/158 |
| 2015/0105604 A1 | | 4/2015 | Liu et al. | |
| 2016/0158578 A1 | * | 6/2016 | Liu | G21K 1/10 600/1 |
| 2018/0001112 A1 | * | 1/2018 | Liu | C04B 35/645 |
| 2018/0172852 A1 | * | 6/2018 | Newman | G01T 1/2008 |
| 2018/0193673 A1 | * | 7/2018 | Liu | H05H 6/00 |
| 2018/0243587 A1 | * | 8/2018 | Liu | A61N 5/10 |
| 2018/0250524 A1 | * | 9/2018 | Liu | G21K 1/067 |
| 2018/0311511 A1 | * | 11/2018 | Liu | A61N 5/10 |
| 2018/0326225 A1 | * | 11/2018 | Liu | G21G 4/02 |
| 2019/0022222 A1 | * | 1/2019 | Chen | C07F 5/02 |
| 2019/0351257 A1 | * | 11/2019 | Chen | G21K 1/10 |
| 2020/0282238 A1 | * | 9/2020 | Liu | A61N 5/1042 |
| 2020/0383198 A1 | * | 12/2020 | Hsueh Liu | H05H 3/06 |
| 2021/0001151 A1 | * | 1/2021 | Liu | A61N 5/1077 |

FOREIGN PATENT DOCUMENTS

| | | |
|---|---|---|
| CN | 106798969 A | 6/2017 |
| EP | 3032926 A1 | 6/2016 |
| EP | 3098209 A1 | 11/2016 |
| JP | 2007242422 A | 9/2007 |
| JP | 2009192488 A | 8/2009 |
| WO | 2017118291 A1 | 7/2017 |
| WO | 2017146205 A1 | 8/2017 |
| WO | 2017164408 A1 | 9/2017 |

* cited by examiner

NEUTRON CAPTURE THERAPY SYSTEM

CROSS-REFERENCE TO RELATED PATENT APPLICATION

This application is a continuation application of International Application No. PCT/CN2018/100787, filed on Aug. 16, 2018, which claims priority to Chinese Patent Application No. 201711347618.5, filed on Dec. 15, 2017, and Chinese Patent Application No. 201721763785.3, filed on Dec. 15, 2017, the disclosures of which are hereby incorporated by reference.

FIELD

The present disclosure relates to a radioactive irradiation system, and more particularly to a neutron capture therapy system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

As atomics moves ahead, radiotherapy such as Cobalt-60 therapy, linear accelerator therapy and electron beam therapy has been one of the major approaches to cancer treatment. However, conventional photon or electron therapy has undergone physical restrictions of radioactive rays. For example, a large amount of normal tissue on a beam path is damaged as tumor cells are killed. Moreover, tumor cells have different radiosensitivities, and as a result conventional radiotherapy falls short of treatment effectiveness on radioresistant malignant tumors (such as glioblastoma multiforme and melanoma).

To reduce radiation damage to the normal tissue surrounding a tumor, targeted therapy in chemotherapy has been applied to radiotherapy. For highly radioresistant tumor cells, proton therapy, heavy particle therapy, neutron capture therapy, and the like using a radiation source with high relative biological effectiveness (RBE) are being actively developed at present. Among them, the neutron capture therapy combines the target therapy with the RBE. For example, the boron neutron capture therapy (BNCT). The boron neutron capture therapy provide a better cancer treatment option than conventional radiotherapy by specific grouping of boron-containing drugs in tumor cells is combined with precise neutron beam regulation to.

The effect of BNCT depends on the concentration of boron-containing drugs and the quantity of thermal neutrons in the tumor cells, so it is also referred to as binary cancer therapy. It may be seen that in addition to the development of boron-containing drugs, the improvement in the fluxes and quality of neutron sources plays a significant role in the research of BNCT.

In addition, a variety of radioactive rays are generated during radiotherapy, for example, low-energy to high-energy neutrons and photons, these radioactive rays may cause different levels of damage to normal tissue of a human body. Therefore, in the field of radiotherapy, how to provide effective treatment while reducing radiation pollution to external environment, medical workers and normal tissue of a patient is a vital subject.

Therefore, it is necessary to propose a new technical solution to resolve the foregoing problem.

SUMMARY

To resolve the foregoing problem, one aspect of the present disclosure provides a neutron capture therapy system. The neutron capture therapy system includes a beam shaping assembly and a vacuum tube disposed in the beam shaping assembly. the beam shaping assembly, comprising a beam entrance, an accommodating cavity for accommodating the vacuum tube, a moderator adjacent to an end of the accommodating cavity, a reflector surrounding the moderator, a radiation shield disposed in the beam shaping assembly, and a beam exit, wherein the moderator moderates neutrons generated from a target to an epithermal neutron energy range, the reflector guides deflecting neutrons back to the moderator to enhance an intensity of an epithermal neutron beam, the radiation shield is configured to shield against leaked neutrons and photons to reduce a dose to a normal tissue in a non-irradiation area. The target is disposed at an end of the vacuum tube, the target undergoes a nuclear reaction with a charged particle beam entering through the beam entrance to generate neutrons, the neutrons form a neutron beam, and the neutron beam is emitted from the beam exit and defines a neutron beam axis. The moderator at least comprises two cylindrical moderating members with different outer diameters respectively, the moderator has a first end close to the beam entrance and a second end close to the beam exit, and the target is accommodated between the first end and the second end.

Compared with the related art, the technical solution disclosed in this embodiment has the following beneficial effects: The moderator at least includes two cylindrical moderating members with different outer diameters respectively, and the target is accommodated in the moderator, which can reduce the material costs, greatly reduce the intensity of fast neutrons, and improve the neutron beam quality.

Preferably, the moderator comprises a first moderating unit close to the beam entrance and a second moderating unit closely attached to the first moderating unit and close to the beam exit, the first moderating unit at least comprises two cylindrical moderating members with different outer diameters respectively, wherein all of the beam entrance, the moderator and the beam exit are extended along the neutron beam axis, and wherein a distance from the target to the beam exit is less than a distance from the first end to the beam exit.

Further, the first moderating unit comprises three cylindrical moderating members with different outer diameters respectively, the first moderating unit comprises a first moderating portion close to the beam entrance, a second moderating portion closely attached to the first moderating portion, and a third moderating portion closely attached to the second moderating portion, the first moderating portion, the second moderating portion and the third moderating portion are sequentially arranged along an axial direction of the neutron beam, the first moderating portion defines a first outer diameter, the second moderating portion defines a second outer diameter greater than the first outer diameter, the third moderating portion defines a third outer diameter greater than the second outer diameter, the second moderating unit defines a fourth outer diameter equal to the third outer diameter.

Preferably, the first moderating portion comprises a first front end surface close to the beam entrance, a first rear end surface close to the beam exit and a first outer circumferential surface, the second moderating portion comprises a second front end surface closely attached to the first rear end surface, a second rear end surface close to the beam exit and a second outer circumferential surface, the third moderating portion comprises a third front end surface closely attached to the second rear end surface, a third rear end surface close to the beam exit and a third outer circumferential surface, the second moderating unit comprises a fourth front end surface closely attached to the third rear end surface, a fourth rear end surface close to the beam exit and a fourth outer circumferential surface, in the tangent surface passing through the neutron beam axis, the first front end surface intersects the first outer circumferential surface to obtain a first intersection point, the second front end surface intersects the second outer circumferential surface to obtain a second intersection point, the third front end surface intersects the third outer circumferential surface to obtain a third intersection point, and the first intersection point, the second intersection point and the third intersection point are located on a same straight line or one arc lin.

Further, a reflection compensator is filled between the accommodating cavity and the vacuum tube, and the reflection compensator is lead or Al or Teflon or C.

Further, the first end protrudes from the target along the neutron beam axis in a direction towards the beam entrance, and the second end protrudes from the target along the neutron beam axis in a direction towards the beam exit.

Further, the reflector protrudes from the moderator on both sides of the neutron beam axis, the accommodating cavity comprises a reflector accommodating cavity surrounded by the reflector and a moderator accommodating cavity extending from the reflector accommodating cavity and surrounded by the moderator, the vacuum tube comprises an extending section accommodated in the reflector accommodating cavity and an insertion section extending from the extending section and accommodated in the moderator accommodating cavity, and the target is disposed at an end of the insertion section.

Further, the neutron capture therapy system further comprises at least one cooling device, at least one accommodating pipe disposed in the beam shaping assembly for accommodating the cooling device and a lead alloy or an aluminum alloy filled between the cooling device and an inner wall of the accommodating pipe.

Further, the neutron capture therapy system further comprises a shielding assembly disposed at the beam entrance and closely attached to the beam shaping assembly.

Further, a cross section of the second moderating unit is conical or cylindrical or steped-shaped.

Further, a depth of the target entering into the moderator is less than or equal to a length of the first moderating unit in an axial direction of the neutron beam.

Further, the cooling device comprises a first cooling portion arranged in a vertical direction and located in front of the target for cooling the target and a second cooling portion and a third cooling portion extending in an axial direction of the neutron beam and respectively located on two sides of the vacuum tube, the first cooling portion is connected between the second cooling portion and the third cooling portion, the second cooling portion inputs a cooling medium into the first cooling portion, and the third cooling portion outputs the cooling medium in the first cooling portion.

In another aspect of the present disclosure provides a neutron capture therapy system. The neutron capture therapy system includes a beam shaping assembly, a vacuum tube disposed in the beam shaping assembly and a target disposed at an end of the vacuum tube. The target undergoes a nuclear reactions with a charged particle beam entering through the beam entrance to generate neutrons. The beam shaping assembly includes a beam entrance, an accommodating cavity for accommodating the vacuum tube, a moderator adjacent to an end of the accommodating cavity, a reflector surrounding the moderator and a beam exit. The moderator at least comprises two hollow cylindrical moderating members with different outer diameters and same inner diameter respectively.

Further, a reflection compensator is filled between the accommodating cavity and the vacuum tube, and the reflection compensator is lead or Al or Teflon or C.

Further, the neutron capture therapy system further comprises at least one cooling device, at least one accommodating pipe disposed in the beam shaping assembly for accommodating the cooling device, and a lead alloy or an aluminum alloy is filled between the cooling device and an inner wall of the accommodating pipe.

Further, the moderator comprises a first end close to the beam entrance and a second end close to the beam exit, and the target is accommodated between the first end and the second end.

In yet another aspect of the present disclosure provides a neutron capture therapy system. The neutron capture therapy system includes a beam shaping assembly. The a beam shaping assembly includes a beam entrance, a moderator, a reflector surrounding the moderator, and a beam exit. The moderator at least comprises two hollow cylindrical moderating members with different outer diameters respectively.

Further, the moderator comprises a first moderating unit close to the beam entrance and a second moderating unit closely attached to the first moderating unit and close to the beam exit, the first moderating unit at least comprises two hollow cylindrical moderating members with different outer diameters respectively.

Further, the neutron capture therapy system further comprises at least one cooling device, at least one accommodating pipe disposed in the beam shaping assembly for accommodating the cooling device and a lead alloy or an aluminum alloy filled between the cooling device and an inner wall of the accommodating pipe.

Further, the neutron capture therapy system further comprises a vacuum tube disposed in the beam shaping assembly, the beam shaping assembly further comprises an accommodating cavity for accommodating the vacuum tube, a reflection compensator is filled between the accommodating cavity and the vacuum tube, and the reflection compensator is lead or Al or Teflon or C.

The "cone" or "conical body" in the embodiments of the present disclosure is a structure with an overall outer contour gradually becoming smaller from one side to the other in a direction in the drawings. The entire surface of the outer contour may have a smooth transition or may have nonsmooth transition. For example, many protrusions and grooves are provided in the surface of the conical body.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

Figure 1:
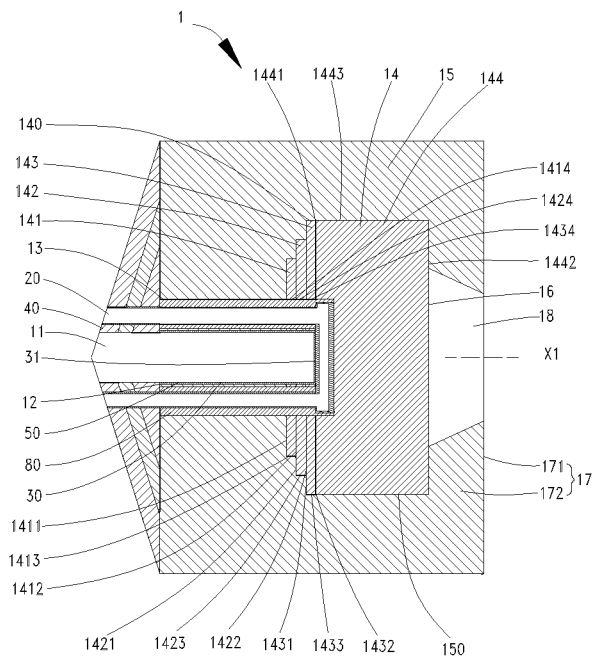
FIG. 1 is a schematic diagram of a neutron capture therapy system according to a first embodiment of the present disclosure, where a second cooling portion and a third cooling portion of a cooling device are parallel to a neutron beam axis.

The embodiments of the present disclosure are further described in detail below with reference to the accompanying drawings, so that those skilled in the art can implement the technical solutions according to the description.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components comprise, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7Li$ (p, n)$^7Be$ and $^9Be$ (p, n)$^9B$ and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. The target in these embodiments of the present disclosure is made of lithium. However, well known by those skilled in the art, the target materials may be made of other metals besides the above-mentioned.

Requirements for the heat removal system differ as the selected nuclear reactions. $^7Li$ (p, n)$^7Be$ asks for more than $^9Be$ (p, n)$^9B$ does because of low melting point and poor thermal conductivity coefficient of the metal (lithium) target. In these embodiments of the present disclosure is $^7Li$ (p, n)$^7Be$. It may be seen that the temperature of the target that is irradiated by an accelerated charged particle beam at a high energy level inevitably rises significantly, and as a result the service life of the target is affected.

No matter BNCT neutron sources are from the nuclear reactor or the nuclear reactions between the accelerator charged particles and the target, only mixed radiation fields are produced, that is, beams comprise neutrons and photons having energies from low to high. As for BNCT in the depth of tumors, except the epithermal neutrons, the more the residual quantity of radiation ray is, the higher the proportion of nonselective dose deposition in the normal tissue is. Therefore, radiation causing unnecessary dose should be lowered down as much as possible. Besides air beam quality factors, dose is calculated using a human head tissue prosthesis in order to understand dose distribution of the neutrons in the human body. The prosthesis beam quality factors are later used as design reference to the neutron beams, which is elaborated hereinafter.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux >1×10$^9$ n/cm$^2$ s
Fast neutron contamination <2×10$^{-13}$ Gy-cm$^2$/n
Photon contamination <2×10$^{-13}$ Gy-cm$^2$/n
Thermal to epithermal neutron flux ratio <0.05
Epithermal neutron current to flux ratio >0.7

Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than $10^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons are considered as contamination. The dose exhibit positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than $2*10^{-13}$Gy-cm$^2$/n.

3. Photon Contamination (Gamma-Ray Contamination)

Gamma-ray long-range penetration radiation will selectively result in dose deposit of all tissues in beam paths, so that lowering the quantity of gamma-ray is also the exclusive requirement in neutron beam design. Gamma-ray dose accompanied per unit epithermal neutron flux is defined as gamma-ray contamination which is suggested being less than $2*10^{-13}$Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

To reduce the manufacturing costs of a beam shaping assembly of a neutron capture therapy system and obtain relatively good neutron beam quality, referring to FIG. 1, a first embodiment of the present disclosure provides a neutron capture therapy system 1. The neutron capture therapy system 1 includes a beam shaping assembly 10, a cooling device 20 disposed in the beam shaping assembly 10, a vacuum tube 30, and a shielding assembly 40 disposed outside of the beam shaping assembly 10 and closely attached to the beam shaping assembly 10.

Figure 2:
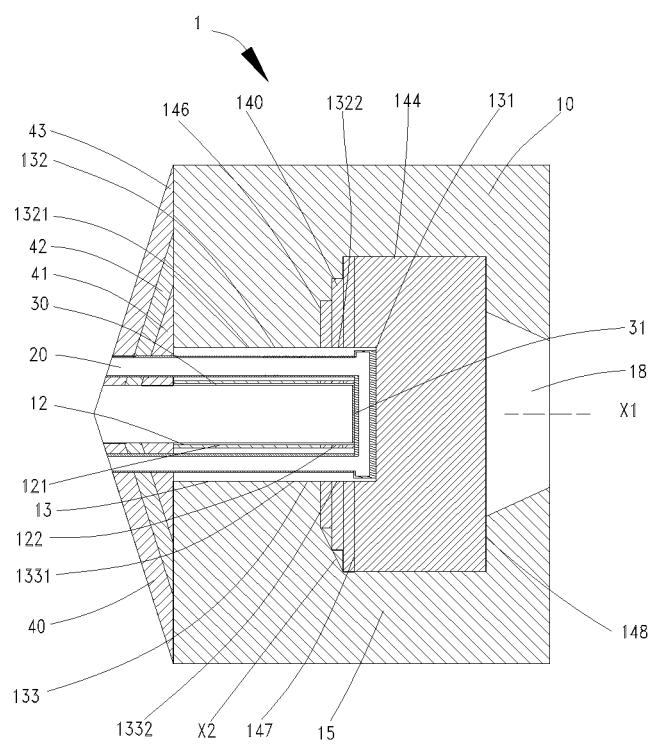
FIG. 2 is a schematic diagram of the neutron capture therapy system in which a reflection compensator and a reflection compensation material are not filled according to the first embodiment of the present disclosure.

As shown in FIG. 1 and FIG. 2, the beam shaping assembly 10 includes a beam entrance 11, an accommodating cavity 12 configured to accommodate the vacuum tube 30, an accommodating pipe 13 configured to accommodate the cooling device 20, a moderator 14 adjacent to an end of the accommodating cavity 12, a reflector 15 surrounding the moderator 14, a thermal neutron absorber 16 adjacent to the moderator 14, a radiation shield 17 disposed in the beam shaping assembly 10, and a beam exit 18. A target 31 is disposed at an end of the vacuum tube 30. A nuclear reaction occur between the target 31 and a charged particle beam that enters through the beam entrance 11 and passes through the vacuum tube 30 to generate neutrons, the neutrons form the neutron beam, and the neutron beam is emitted from the beam exit 18 and defines a neutron beam axis X1 that coincides with the central axis of the vacuum tube 30. The moderator 14 moderates the neutrons generated from the target 31 to an epithermal neutron energy range, and the reflector 15 leads neutrons deflected from the neutron beam axis X1 back to the moderator 14 to enhance the intensity of an epithermal neutron beam. The reflector 15 protrudes from the moderator 14 on both sides of the neutron beam axis X1. The thermal neutron absorber 16 is configured to absorb thermal neutrons to protect superficial normal tissue from an overdose during treatment. The radiation shield 17 is configured to shield against leaked neutrons and photons to reduce a dose to a normal tissue in a non-irradiation area.

Figure 7:
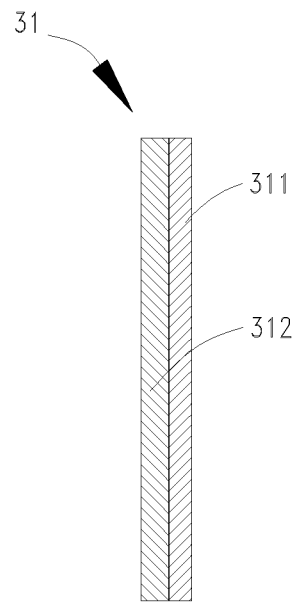
FIG. 7 is a schematic structural diagram of a target in a neutron capture therapy system according to an embodiment of the present disclosure.

In an accelerator-based neutron capture therapy system, an accelerator accelerates the charged particle beam. In one embodiment, the target 31 is made of lithium metal. Specifically, the target 31 is made of lithium metal in which the content of $^7$Li is 98% and the content of $^6$Li is 2%. The charged particle beam is accelerated to an energy sufficient to overcome the energy of the coulomb repulsion of atomic nuclei of the target, and the $^7$Li (p, n)$^7$Be nuclear reaction occurs between the charged particle beam and the target 31 to generate neutrons. The beam shaping assembly 10 can moderate the neutrons to the epithermal neutron energy range, and reduce the content of thermal neutrons and fast neutrons. The moderator 14 is made of a material with a large fast neutron reaction cross section and a small epithermal neutron reaction cross section, the reflector 15 is made of a material with high neutron reflectivity, the thermal neutron absorber 16 is made of a material with a large thermal neutron reaction cross section. In one embodiment, the moderator 14 is made of a mixture of MgF$_2$ and LiF that is accounts for 4.6% of MgF$_2$ by weight, the reflector 15 is made of Pb, and the thermal neutron absorber 16 is made of $^6$Li. The radiation shield 17 includes a photon shielding 171 and a neutron shielding 172. In one embodiment, the photon shielding 171 made of lead (Pb) and the neutron shielding 172 made of polyethylene (PE). As shown in FIG. 7, the target 31 includes a lithium target layer 311 and an antioxidation layer 312 that is located on a side of the lithium target layer 311 and is configured to prevent the lithium target layer 311 from oxidating. The antioxidation layer 312 of the target 31 is made of Al or stainless steel.

As shown in FIG. 1 and FIG. 2, the moderator 14 includes a first moderating unit 140 close to the beam entrance 11 and a second moderating unit 144 that is closely attached to the first moderating unit 140 and is close to the beam exit 18. The moderator 14 has a first end 146 close to the beam entrance 11, a second end 148 close to the beam exit 18, and a third end 147 that is located between the first end 146 and the second end 148. The third end 147 is located between the first moderating unit 140 and the second moderating unit 144. The beam entrance 11, the moderator 14, and the beam exit 18 all extend along the neutron beam axis X1. A distance from the target 31 to the beam exit 18 is less than a distance from the first end 146 to the beam exit 18. In other words, the first end 146 protrudes from the target 31 along a neutron beam axis X1 in a direction towards the beam entrance 11, and the second end 148 protrudes from the target 31 along the neutron beam axis X1 in a direction towards the beam exit 18. The first moderating unit 140 includes at least two hollow cylindrical moderating members with different outer diameters and the same inner diameter, respectively. Referring to FIG. 1, FIG. 2, FIG. 6, and FIG. 8, in the first embodiment, a third embodiment, and a fourth embodiment, the first moderating unit 140 includes three hollow cylindrical moderating members with different outer diameters and the same inner diameter, respectively. The first moderating unit 140 and the second moderating unit 144 are formed by stacking and splicing several moderating members formed from molds with corresponding sizes and then subjected to processes such as polishing, grinding, Specifically, the first moderating unit 140 includes a first moderating portion 141 close to the beam entrance 11, a second moderating portion 142 that is located on the right side of the first moderating portion 141 and closely attached to the first moderating portion 141, and a third moderating portion 143 that is located on the right side of the second moderating portion 142 and closely attached to the second moderating portion 142. That is, the first moderating portion 141, the second moderating portion 142, and the third moderating portion 143 are sequentially arranged along a direction of the neutron beam axis X1. The first moderating portion 141 defines a first outer diameter, the second moderating portion 142 defines a second outer diameter greater than the first outer diameter, the third moderating portion 143 defines a third outer diameter greater than the second outer diameter, the second moderating unit 144 defines a fourth outer diameter equal to the third outer diameter, and inner diameters of the first moderating portion 141, the second moderating portion 142, and the third moderating portion 143 are equal. The central axes of the first moderating portion 141, the second moderating portion 142, and the third moderating portion 143 coincide with the centerline of the second moderating unit 144. The central axes also coincide with the neutron beam axis X1. The first moderating portion 141 has a first front end surface 1411 located on the left side, a first rear end surface 1412 located on the right side, a first outer circumferential surface 1413, and a first inner circumferential surface 1414. The second moderating portion 142 has a second front end surface 1421 located on the left side, a second rear end surface 1422 located on the right side, a second outer circumferential surface 1423, and a second inner circumferential surface 1424. The third moderating portion 143 has a third front end surface 1431 located on the left side, a third rear end surface 1432 located on the right side, a third outer circumferential surface 1433, and a third inner circumferential surface 1434. The second moderating unit 144 has a fourth front end surface 1441 located on the left side, a fourth rear end surface 1442 located on the right side, and a fourth outer circumferential surface 1443. All of the first front end surface 1411, the second front end surface 1421, the third front end surface 1431, the fourth front end surface 1441, the first rear end surface 1412, the second rear end surface 1422, the third rear end surface 1432, and the fourth rear end surface 1442 are parallel to each other and are perpendicular to the neutron beam axis X1. The first rear end surface 1412 of the first moderating portion 141 is closely attached to the second front end surface 1421 of the second moderating portion 142, the second rear end surface 1422 of the second moderating portion 142 is closely attached to the third front end surface 1431 of the third moderating portion 143, and the third rear end surface 1432 of the third moderating portion 143 is closely attached to the fourth front end surface 1441 of the second moderating unit 144. An intersection line of the tangent surface passing through the neutron beam axis X1 and the first outer circumferential surface 1413 is perpendicular to the second front end surface 1421, an intersection line of the tangent surface passing through the neutron beam axis X1 and the second outer circumferential surface 1423 is perpendicular to the third front end surface 1431, and there is smooth transition between the third outer circumferential surface 1433 of the third moderating portion 143 and the fourth outer circumferential surface 1443 of the second moderating unit 144. As shown in FIG. 2, in the tangent surface passing through the neutron beam axis X1, the first front end surface 1411 intersects the first outer circumferential surface 1413 of the first moderating portion 141 to obtain a first intersection point 1410, the second front end surface 1421 of the second moderating portion 142 intersects the second outer circumferential surface 1423 to obtain a second intersection point 1420, the third front end surface 1431 of the third moderating portion 143 intersects the third outer circumferential surface 1433 to obtain a third intersection point 1430, the first intersection point 1410, the second intersection point 1420, and the third intersection point 1430 are located on a same straight line X2, and an angle between the straight line X2 and the neutron beam axis X1 is less than 90 degrees. The reflector 15 has an inner surface 150 surrounding the moderator 14, and the inner surface 150 is closely attached to the first front end surface 1411, the first outer circumferential surface 1413, the second front end surface 1421, the second outer circumferential surface 1423, the third front end surface 1431, the third outer circumferential surface 1433, the fourth rear end surface 1442, and the fourth outer circumferential surface 1443 of the moderator 14.

Figure 10:
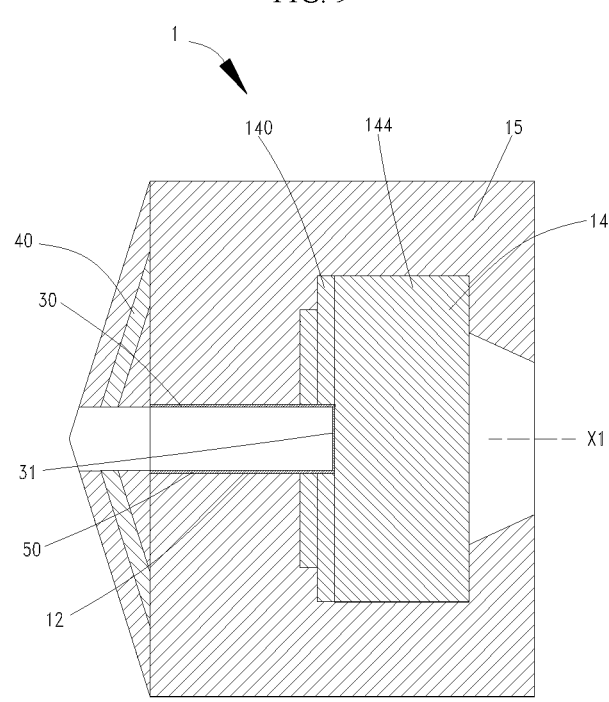
FIG. 10 is a schematic diagram of a neutron capture therapy system in which a cooling device is removed and a first moderating unit is a two-step moderator according to a sixth embodiment of the present disclosure.
Figure 11:
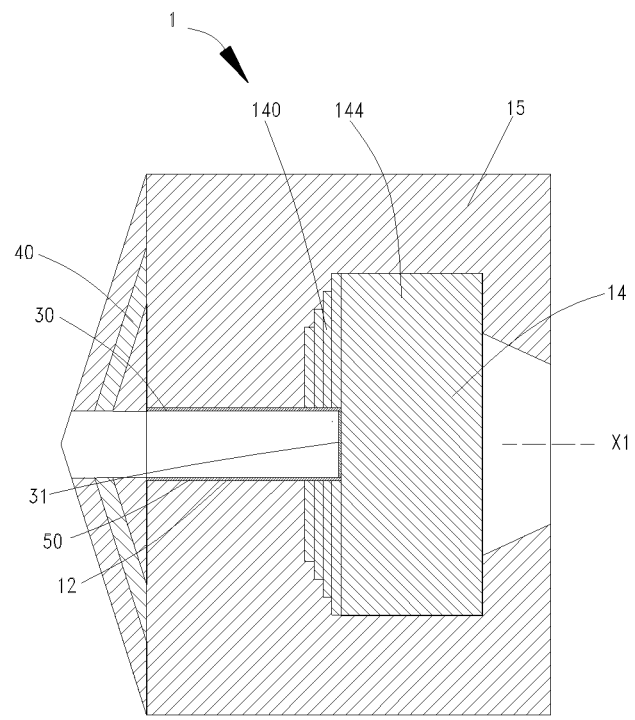
FIG. 11 is a schematic diagram of a neutron capture therapy system in which a cooling device is removed and a first moderating unit is a four-step moderator according to a seventh embodiment of the present disclosure.
Figure 12:
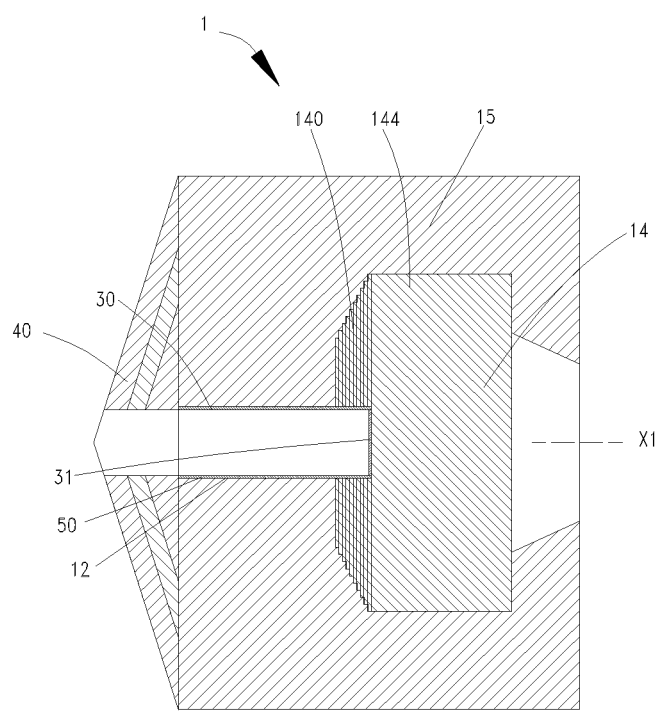
FIG. 12 is a schematic diagram of a neutron capture therapy system in which a cooling device is removed and a first moderating unit is a ten-step moderator according to an eighth embodiment of the present disclosure.

As shown in FIG. 1, FIG. 2, FIG. 6, and FIG. 8, in the first embodiment, the third embodiment, and the fourth embodiment, the first moderating unit 140 includes three concentric hollow cylindrical moderating members with different outer diameters and the same inner diameter, respectively. As observed along a direction perpendicular to the neutron beam axis X1, outer contours of the first moderating portion 141, the second moderating portion 142, and the third moderating portion 143 are combined to form a step shape, therefore, the first moderating unit 140 is named a three-step moderator. As shown in FIG. 10 to FIG. 12, from sixth embodiment to eighth embodiment, the first moderating unit 140 includes two, four, ten hollow cylindrical moderating members with different outer diameters and the same inner diameter, respectively. That is, the first moderating unit 140 may be a two-step moderator, four-step moderator, ten-step moderator. In another embodiment, the first moderating unit 140 may further includes another quantity of hollow cylindrical moderating members with different outer diameters and the same inner diameter, respectively. For example, twelve cylindrical moderating members, fifteen cylindrical moderating members, and the like. In another embodiment, the second moderating unit 144 may also be disposed to be a steped-shaped moderator. Alternatively, a polygonal prism may be used in place of a cylinder to form the moderator. In addition, the first intersection point 1410, the second intersection point 1420, and the third intersection point 1430 may be located on one arc line instead of the straight line X2. In addition, according to an actual requirement, the moderating portion that form the first moderating unit 140 may be disposed to have a partially non-hollow structure. The central axes of the moderating portion of the first moderating unit 140 may not coincide with the central axis of the second moderating unit 144.

Generally, the moderator is formed by stacking and splicing several moderating members that are formed from molds with corresponding sizes and then subjected to processes such as polishing, grounding. The moderator formed from the mold is disc-shaped. When the moderator is designed as an entire cylinder or cone, the volume of the moderator material consumed is a product of the size of the moderator in the direction of the neutron beam axis X1 and the bottom area of the disk. It should be noted that the conical moderator is obtained by grinding the cylindrical moderator. That is, the volume of material needed for the design of the moderator to be cylindrical or conical is the same. In the present disclosure, the first moderating unit 140 is designed to be a step-shaped moderator. On the premise that the size of the moderator in the direction of the neutron beam axis X1 and the maximum diameter of the moderator are remain unchanged, because the bottom areas of the disc-shaped moderator forming the steped-shaped moderator is gradually increasing, in the present disclosure, the moderator material needed when the moderator is designed to be the steped-shaped moderator is less than the material needed when the moderator is designed to be the entire cylindrical moderator or conical moderator. As can be learned, the steped-shaped moderator in the present disclosure can greatly reduce the material for manufacturing the moderator, thereby reducing the manufacturing cost.

Referring to FIG. 2, the accommodating cavity 12 is a cylindrical cavity that is surrounded by the reflector 15 and the first moderating unit 140 of the moderator 14. The accommodating cavity 12 includes a reflector accommodating cavity 121 surrounded by the reflector 15 and a moderator accommodating cavity 122 extending from the reflector accommodating cavity 121 and surrounded by the first moderating unit 140 of the moderator 14. That is, the moderator accommodating cavity 122 is surrounded by the first inner circumferential surface 1414 of the first moderating portion 141, the second inner circumferential surface 1424 of the second moderating portion 142, and the third inner circumferential surface 1434 of the third moderating portion 143. The vacuum tube 30 includes an extending section 32 surrounded by the reflector 15 and an insertion section 34 extending from the extending section 32 and inserted into the moderator 14, the extending section 32 is accommodated in the reflector accommodating cavity 121, and the insertion section 34 is accommodated in the moderator accommodating cavity 122. The target 31 is disposed at an end of the insertion section 34 of the vacuum tube 30, and the end is flush with the third rear end surface 1432 of the first moderating unit 140. In the first to third embodiment and fifth to eighth embodiments, the vacuum tube 30 is partially inserted into the moderator 14, that is, the target 31 is disposed in the moderator 14. Mark the depth of the target 31 enters into the moderator 14 as X. The value of X is equal to the size of the moderator accommodating cavity 122 in the direction of the neutron beam axis X1, that is, the size of the first moderating unit 140 in the direction of the neutron beam axis X1.

In another embodiment, the depth X of the target 31 entering into the moderator 14 may be less than or greater than the length of the first moderating unit 140 in the direction along the neutron beam axis X1. That is, along the direction of the neutron beam axis X1, the target 31 may be disposed to extend within the first moderating unit 140 or extend beyond the first moderating unit 140 and into the second moderating unit 144. Correspondingly, when the target 31 is disposed to extend within the first moderating unit 140 along the direction of the neutron beam axis X1, the first moderating unit 140 is disposed to have a partially non-hollow structure. When the target 31 is disposed to extend beyond the first moderating unit 140 and into the second moderating unit 144 along the direction of the neutron beam axis X1, the first moderating unit 140 is disposed to have a hollow structure, and the second moderating unit 144 is disposed to have a partially hollow structure.

Figure 3:
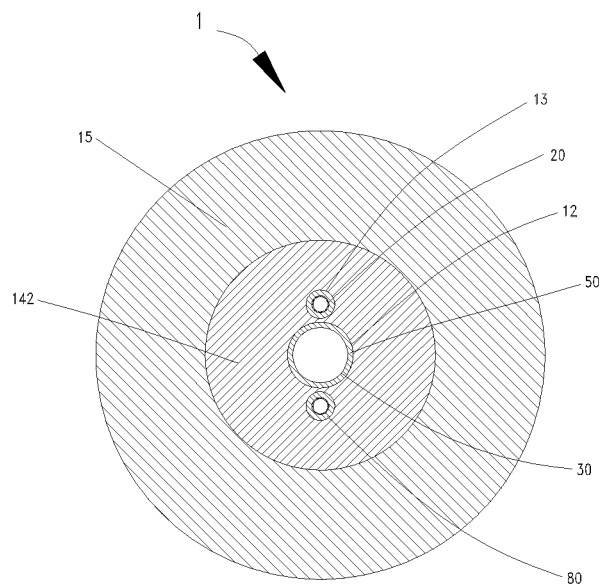
FIG. 3 is a sectional view in a direction that is perpendicular to the neutron beam axis and passes through a second moderating unit of the neutron capture therapy system in FIG. 1 according to the first embodiment of the present disclosure.

Referring to FIG. 1, FIG. 2, and FIG. 3, a gap exists between the accommodating cavity 12 and the vacuum tube 30, a reflection compensator 50 is filled in the gap, and the reflection compensator 50 is Pb or Al or Teflon or carbon that can absorb or reflect neutrons. The reflection compensator 50 can reflect neutrons reflected or scattered into the gap into the moderator 14 or the reflector 15, thereby increasing the intensity of epithermal neutrons and reducing the time that an irradiated body needs to be irradiated. In another aspect, it avoids leakage of neutrons to the outside of the beam shaping assembly 10 to cause adversely affect to the instruments of the neutron capture therapy system, and improves radiation safe.

As shown in FIG. 1 and FIG. 2, the accommodating pipe 13 includes a second accommodating pipe 132 and a third accommodating pipe 133 that extend along the direction of the neutron beam axis X1 and are respectively located on two sides of the accommodating cavity 12 at 180° intervals and a first accommodating pipe 131 that is disposed in a plane perpendicular to the neutron beam axis X1 and is located between the target 31 and the moderator 14. The second accommodating pipe 132 and the third accommodating pipe 133 extend beyond the accommodating cavity 12 in the direction of the neutron beam axis X1 and communicate with the first accommodating pipe 131 respectively. That is, the first accommodating pipe 131 is located at an end of the accommodating cavity 12 and between the target 31 and the moderator 14, and the second accommodating pipe 132 and the third accommodating pipe 133 are respectively located on two sides of the accommodating cavity 12 and are respectively communicated with the first accommodating pipe 131, so that the accommodating pipe 30 is arranged in a "["-shaped structure. Referring to FIG. 2, the second accommodating pipe 132 and the third accommodating pipe 133 respectively include a second reflector accommodating pipe 1321 and a third reflector accommodating pipe 1331 located on an outer side of the reflector accommodating cavity 121 and a second moderating unit accommodating pipe 1322 and a third moderator accommodating pipe 1332 extending from the second reflector accommodating pipe 1321 and the third reflector accommodating pipe 1331 and located on the outer side of the moderator accommodating cavity 122, respectively. In this embodiment, the second accommodating pipe 132 and the third accommodating pipe 133 extend in the direction along the neutron beam axis X1 and are parallel to the neutron beam axis X1. That is, an angle between the second accommodating pipe 132 and the third accommodating pipe 133 and the neutron beam axis X1 is 0°.

In the first embodiment and the second embodiment, the second accommodating pipe 132 and the third accommodating pipe 133 are not in communication with the accommodating cavity 12, that is, the second accommodating pipe 132 and the third accommodating pipe 133 are separated from the accommodating cavity 12 by the reflector 15 and the moderator 14. In another embodiment, the second accommodating pipe 132 and the third accommodating pipe 133 may be in communication with the accommodating cavity 12, that is, an outer surface the vacuum tube 30 accommodated in the accommodating cavity 12 is partially exposed in the second accommodating pipe 132 and the third accommodating pipe 133. In conclusion, the second accommodating pipe 132 and the third accommodating pipe 133 are located outside an inner wall of the accommodating cavity 12. In this embodiment of the present disclosure, the second accommodating pipe 132 and the third accommodating pipe 133 are disposed to be arc-shaped pipes extending along an axial direction of the vacuum tube 30, in another embodiments, the second accommodating pipe 132 and the third accommodating pipe 133 may be disposed to be rectangular pipes, triangular pipes or another polygonal pipes. In this embodiment of the present disclosure, the second accommodating pipe 132 and the third accommodating pipe 133 are two independent accommodating pipes that are separated in a circumferential direction of the accommodating cavity 12. In another embodiments, the second accommodating pipe 132 and the third accommodating pipe 133 are in communication with each other in the circumferential direction of the accommodating cavity 12, that is, the second accommodating pipe 132 and the third accommodating pipe 133 are replaced with one accommodating pipe surrounding the accommodating cavity 12.

Figure 5:
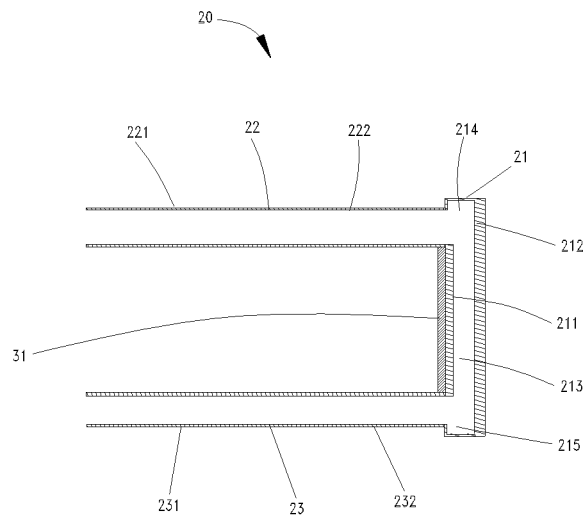
FIG. 5 is a schematic partial enlarged view of a cooling device of the neutron capture therapy system according to the first embodiment and a second embodiment of the present disclosure.

As shown in FIG. 5, the cooling device 20 includes a first cooling portion 21 arranged in a vertical direction and located in front of the target 31 for cooling the target 31 and a second cooling portion 22 and a third cooling portion 23 extending in the direction of the neutron beam axis X1 and respectively located on two sides of the vacuum tube 30 and parallel to the neutron beam axis X1. The first cooling portion 21 is connected between the second cooling portion 22 and the third cooling portion 23. The first cooling portion 21 is accommodated in the first accommodating pipe 131 arranged in the direction perpendicular to the neutron beam axis X1, and the second cooling portion 22 and the third cooling portion 23 are respectively accommodated in the second accommodating pipe 132 and the third accommodating pipe 133 arranged in the direction of the neutron beam axis X1. The second cooling portion 22 inputs a cooling medium into the first cooling portion 21, and the third cooling portion 23 outputs the cooling medium in the first cooling portion 21. The first cooling portion 21 is located between the target 31 and the moderator 14. One side of the first cooling portion 21 is in direct contact with the target 31, and the other side of the first cooling portion 21 is in contact with the moderator 14. The second cooling portion 22 and the third cooling portion 23 respectively include a first cooling section 221 and a second cooling section 231 located on the outer side of the reflector accommodating cavity 121 and a third cooling section 222 and a fourth cooling section 232 respectively extending from the first cooling section 221 and the second cooling section 231 and located on the outer side of the moderator accommodating cavity 122. The third cooling section 222 and the fourth cooling section 232 are respectively in communication with the first cooling portion 21. That is, the first cooling portion 21 is located at an end of the insertion section 34 of the vacuum tube 30, and is located on a side of the target 31 and is in direct contact with the target 31, the second cooling portion 22 and the third cooling portion 23 are respectively located on an upper side and a lower side of the vacuum tube 30 accommodated in the accommodating cavity 12 and communicate with the first cooling portion 21, respectively, so that the entire cooling device 20 is disposed to a "["-shaped structure. In this embodiment, the first cooling portion 21 is in plane contact with the target 31, the second cooling portion 22 and the third cooling portion 23 are both tubular structures made of copper, and the second cooling portion 22 and the third cooling portion 23 extend along the direction of the neutron beam axis X1 and are parallel to the neutron beam axis X1, that is, an angle between the neutron beam axis X1 and each of the second cooling portion 22 and the third cooling portion 23 is 0°.

The first cooling portion 21 includes a first contact portion 211, a second contact portion 212, and a cooling groove 213 located between the first contact portion 211 and the second contact portion 212 for passing the cooling medium. The first contact portion 211 is in direct contact with the target 31, and the second contact portion 212 may be in direct contact or may be in indirect contact with the moderator 14 through air. The cooling groove 213 has a input groove 214 communicating with the second cooling portion 22 and a output groove 215 communicating with the third cooling portion 23. The first contact portion 211 is made of a thermally conductive material. An upper edge of the input groove 214 is located above an upper edge of the second cooling portion 22, and a lower edge of the output groove 215 is located below a lower edge of the third cooling portion 23. The benefit of this arrangement is that the cooling device 20 can feed cooling water into the cooling groove 213 more smoothly and cool the target 31 in time, the heated cooling water can also be output from the cooling groove 213 more smoothly, and moreover, the water pressure of cooling water in the cooling groove 213 can further be reduced to a particular degree.

The first contact portion 211 is made of a thermally conductive material (a material such as Cu, Fe, and Al with high thermal conductivity) or a material that can both conduct heat and suppress foaming, the second contact portion 212 is made of a material that suppresses foaming. The material that suppresses foaming or the material that can both conduct heat and suppress foaming is made of any one of Fe, Ta or V. The target 31 is irradiated by accelerated particles at a high energy level, which causes a temperature rise and generate heat, the first contact portion 211 guides out the heat, and the cooling medium that flows in the cooling groove 213 takes away the heat to cool the target 31. In this embodiment, the cooling medium is water.

Referring to FIG. 2, the shielding assembly 40 covers a left end surface of the beam shaping assembly 10 and is closely attached to the end surface to prevent a neutron beam and a γ ray formed at the target 31 from overflowing from the left end surface of the beam shaping assembly 10. The shielding assembly 40 includes Pb and PE. Specifically, the shielding assembly 40 includes at least two layers of Pb and at least one layer of PE. In this embodiment, the shielding assembly 40 includes a first Pb layer 41 closely attached to the left end surface of the beam shaping assembly 10, a PE layer 42 closely attached to the first Pb layer 41, and a second Pb layer 43 covering the PE layer 42 and closely attached to the PE layer 42. Pb can absorb the γ ray overflowing from the beam shaping assembly 10 and reflects neutrons overflowing from the beam shaping assembly 10 back to the moderator 14 to increase the intensity of the epithermal neutron beam.

Figure 4:
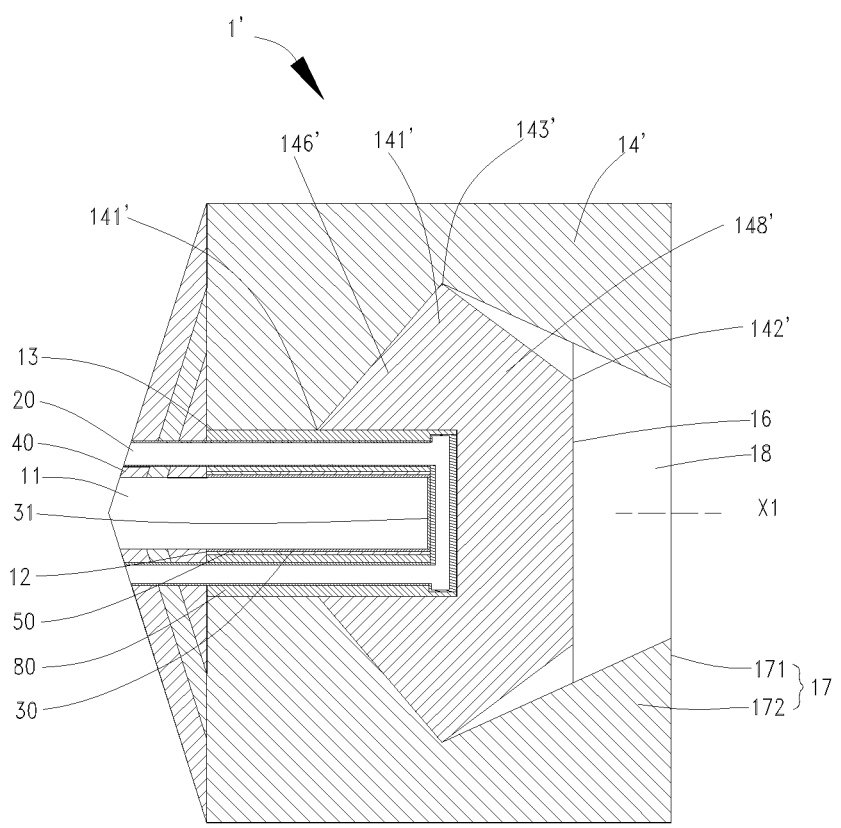
FIG. 4 is a schematic diagram of the neutron capture therapy system according to Embodiment 2 of the present disclosure, where a moderator is disposed to be a double-conical moderator.

Referring to FIG. 1, FIG. 2, FIG. 6, FIG. 8, and FIG. 10 to FIG. 12, in the first embodiment, the third embodiment, the forth embodiment and the sixth embodiment to the eighth embodiment, the moderator 14 part is composed of multi-step moderator. In the fifth embodiment, as shown in FIG. 9, the moderator 14 is composed of an entire cylindrical moderator. In another embodiments, the moderator 14 may be composed of one conical moderator and one cylindrical moderator, or two conical moderator in second embodiment shown in FIG. 4. In second embodiment, a moderator 14' is composed of two opposite conical moderators, and in the present disclosure, the moderator 14' in second embodiment 2 is referred to as a double-conical moderator. Referring to FIG. 4, the moderator 14' has a first end 141', a second end 142', and a third end 143' located between the first end 141' and the second end 142', The cross sections of the first end 141', the second 142', and the third end 143' are circular, and diameters of the first end 141' and the second end 142' are less than the diameter of the third end 143'. A first conical body 146' is formed between the first end 141' and the third end 143', and a second conical body 148' is formed between the third end 143' and the second end 142'. The target 31 is accommodated in the first conical body 146'.

In the second embodiment, an angle between the neutron beam axis X1 and each of the second accommodating pipe 132, the third accommodating pipe 133, the second cooling portion 22, and the third cooling portion 23 is 0°. In another embodiments, the angle between the neutron beam axis X1 and each of the second accommodating pipe 132, the third accommodating pipe 133, the second cooling portion 22, and the third cooling portion 23 may be alternatively any other angle greater than 0° and less than or equal to 180°. For example, as shown in FIG. 6, an angle between the neutron beam axis X1 and each of a second accommodating pipe 132', a third accommodating pipe 133', the second cooling portion 22', and a third cooling portion 23' is 90°.

Figure 6:
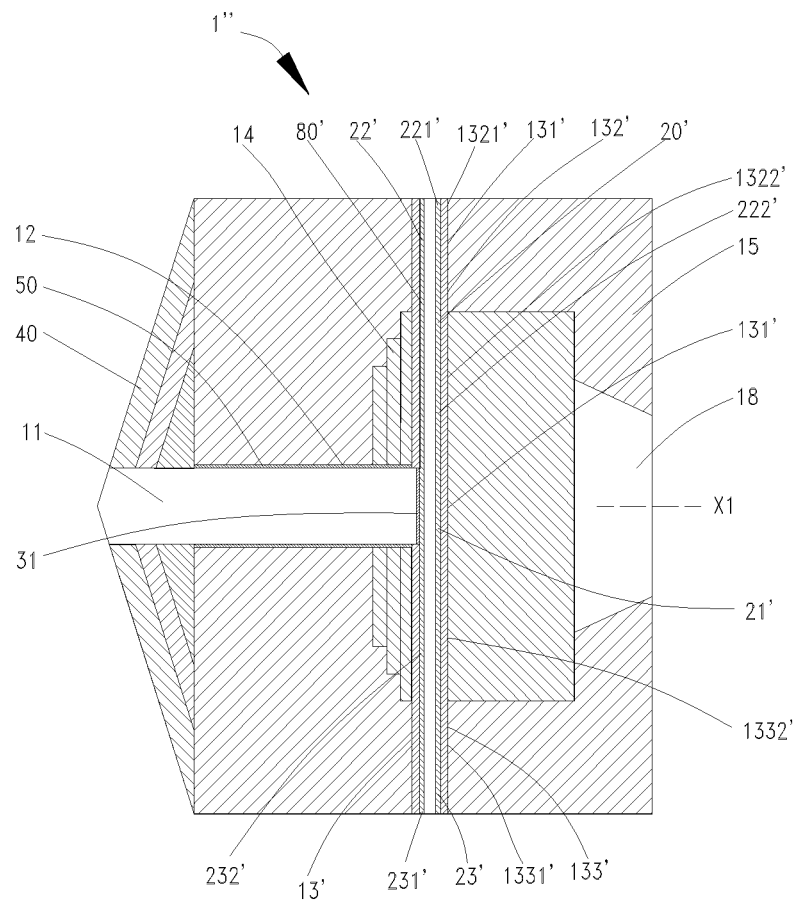
FIG. 6 is a schematic diagram of a neutron capture therapy system according to a third embodiment of the present disclosure, where a second cooling portion and a third cooling portion of a cooling device are perpendicular to a neutron beam axis.

As shown in FIG. 6, it shows a neutron capture therapy system 1" according to the third embodiment of the present disclosure. The second cooling portion 22' and the third cooling portion 23' of a cooling device 20' are perpendicular to the neutron beam axis X1. That is, the cooling device 20' is disposed to an "I"-shaped structure to cool the target 31 in the inserted vacuum tube 30. A first cooling portion 21' in the "I"-shaped cooling device 20' is same as the first cooling portion 21 in the "["-shaped cooling device 20. The difference is that the second cooling portion 22', the third cooling portion 23' and the first cooling portion 21' of the "I"-shaped cooling device 20' are located in the same plane perpendicular to the neutron beam axis X1', and the second cooling portion 22' and the third cooling portion 23' respectively pass through the moderator 14' along the direction perpendicular to the neutron beam axis X1. That is, an angle between the neutron beam axis X1 and each of the second cooling portion 22' and the third cooling portion 23' is 90°, so that the entire cooling device is disposed into a rectangle, that is, the foregoing "I"-shaped structure. Referring to FIG. 6 again, correspondingly, the accommodating pipe 30' is also set to an "I"-shaped structure, the first accommodating pipe 131' of the "I"-shaped accommodating pipe 30' is same as the first accommodating pipe 131 of a "["-shaped cooling pipe 30. Difference is that the second accommodating pipe 132', the third accommodating pipe 133' and the first accommodating pipe 131' of the "I"-shaped accommodating pipe 30' are located in the same plane perpendicular to the neutron beam axis X1, and the second accommodating pipe 132' and the third accommodating pipe 133' respectively pass through the moderator 14' along the direction perpendicular to the neutron beam axis X1. That is, an angle between the neutron beam axis X1 and each of the second accommodating pipe 132' and the third accommodating pipe 133' is 90°, so that the entire accommodating pipe is disposed to be a rectangle, that is, the foregoing "I"-shaped structure. It is readily conceivable that in the structures shown in FIG. 4 and FIG. 9, the cooling device 20 and the accommodating pipe 30 may also be disposed to "I"-shaped structures.

Figure 8:
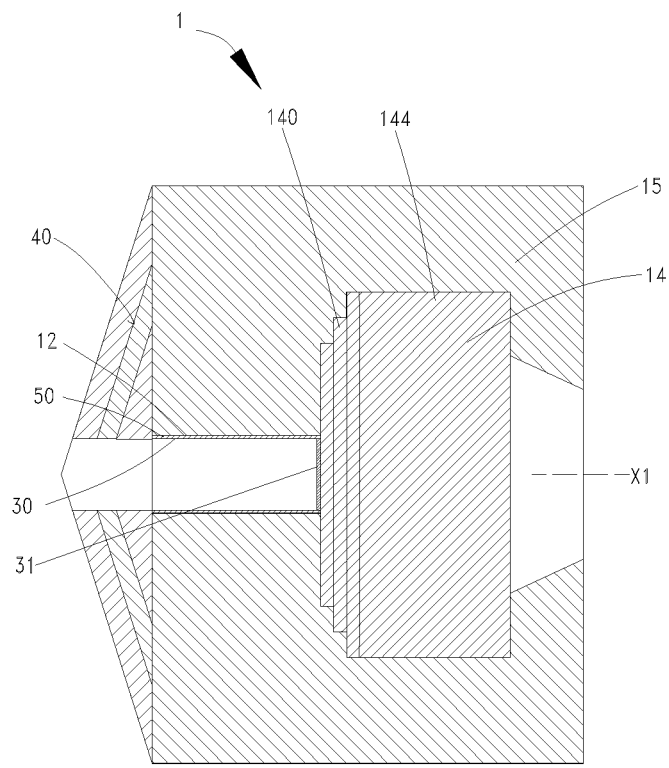
FIG. 8 is a schematic diagram of a neutron capture therapy system in which a cooling device is removed and a target does not enter a moderator according to a fourth embodiment of the present disclosure.
Figure 9:
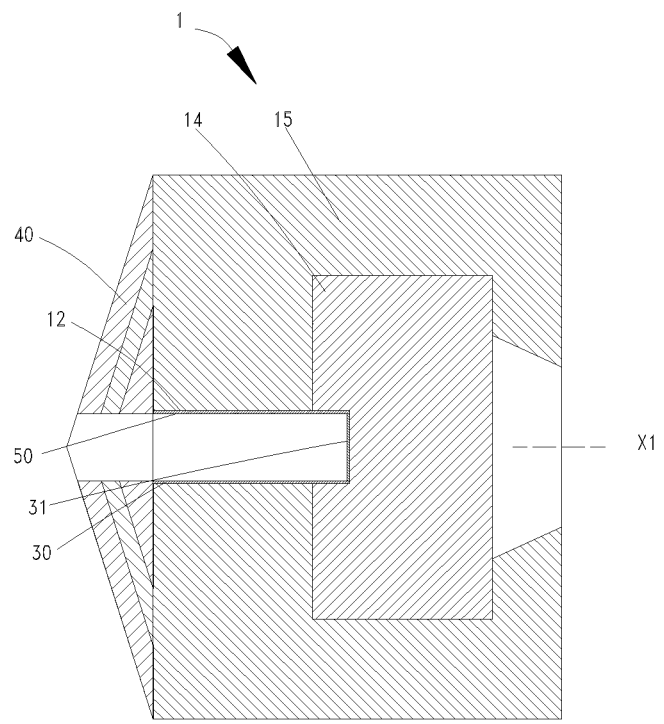
FIG. 9 is a schematic diagram of a neutron capture therapy system in which a cooling device is removed and a first moderating unit is a stepless moderator according to a fifth embodiment of the present disclosure.

FIG. 8 is a schematic diagram of the neutron capture therapy system shown 1 in FIG. 1 or the neutron capture therapy system 1' shown in FIG. 6 in which the cooling device 20, 20' is removed and the target 31 does not insert into the moderator 14. Compared with the neutron capture therapy system 1 disclosed in FIG. 1 or the neutron capture therapy system 1" disclosed in FIG. 6, the neutron capture therapy system 1 disclosed in FIG. 8 only set the target 31 outside the moderator 14. That is, the accommodating cavity 12 for accommodating the vacuum tube 30 does not extend into the moderator 14 but is only surrounded by the reflector 15. The structures of the moderator 14, the reflector 15, the shielding assembly 40, the cooling devices 20, 20', the thermal neutron absorber 16, the radiation shield 17, and the like are the same as the structures disclosed in FIG. 1 or FIG. 6. For related description, please refer to the foregoing description of related structures, details are not described herein again.

FIG. 9 is a schematic diagram of the neutron capture therapy system 1 in which the cooling device 20, 20' is removed and the first moderating unit is a stepless moderator according to the present disclosure. Compared with the neutron capture therapy system 1 disclosed in FIG. 1 or the neutron capture therapy system 1" disclosed in FIG. 6, the neutron capture therapy system 1 disclosed in FIG. 9 only replaces the first moderating unit 140 from a three-step moderator to a stepless moderator. That is, the first moderating unit 140 is composed of a hollow cylindrical second moderating unit with an outer diameter equal to an outer diameter of the cylindrical moderator 144. The structures of the reflector 15, the shielding assembly 40, the cooling devices 20, 20', the thermal neutron absorber 16, the radiation shield 17, and the like are the same as the structures disclosed in FIG. 1 or FIG. 6. For related description, please refer to the foregoing description of related structures, details are not described herein again.

FIG. 10 is a schematic diagram of the neutron capture therapy system 1 in which the cooling device 20, 20' is removed and the first moderating unit is a stepless moderator according to the present disclosure. Compared with the neutron capture therapy system 1 disclosed in FIG. 1 or the neutron capture therapy system 1" disclosed in FIG. 6, the neutron capture therapy system 1 disclosed in FIG. 10 only replaces the first moderating unit 140 from a three-step moderator to a two-step moderator. The structures of the reflector 15, the shielding assembly 40, the cooling devices 20, 20', the thermal neutron absorber 16, the radiation shield 17, and the like are the same as the structures disclosed in FIG. 1 or FIG. 6. For related description, please refer to the foregoing description of related structures, details are not described herein again.

FIG. 11 is a schematic diagram of the neutron capture therapy system 1 in which the cooling device 20, 20' is removed and the first moderating unit is a stepless moderator according to the present disclosure. Compared with the neutron capture therapy system 1 disclosed in FIG. 1 or the neutron capture therapy system 1" disclosed in FIG. 6, the neutron capture therapy system 1 disclosed in FIG. 11 only replaces the first moderating unit 140 from a three-step moderator to a four-step moderator. The structures of the reflector 15, the shielding assembly 40, the cooling devices 20, 20', the thermal neutron absorber 16, the radiation shield 17, and the like are the same as the structures disclosed in FIG. 1 or FIG. 6. For related description, please refer to the foregoing description of related structures, details are not described herein again.

FIG. 12 is a schematic diagram of the neutron capture therapy system 1 in which the cooling device 20, 20' is removed and the first moderating unit is a stepless moderator according to the present disclosure. Compared with the neutron capture therapy system 1 disclosed in FIG. 1 or the neutron capture therapy system 1" disclosed in FIG. 6, the neutron capture therapy system 1 disclosed in FIG. 12 only replaces the first moderating unit 140 from a three-step moderator to a ten-step moderator. The structures of the reflector 15, the shielding assembly 40, the cooling devices 20, 20', the thermal neutron absorber 16, the radiation shield 17, and the like are the same as the structures disclosed in FIG. 1 or FIG. 6. For related description, please refer to the foregoing description of related structures, details are not described herein again.

Referring to FIG. 1, FIG. 2, FIG. 4, and FIG. 6, there is a gap between the second cooling portions 22, 22' and the third cooling portions 23, 23' and inner walls of the second accommodating pipes 132, 132' and the third accommodating pipes 133, 133', respectively. A reflection compensator 80, 80' are filled in the gaps, respectively. The reflection compensator 80, 80' are substances such as a lead alloy or an aluminum alloy that can absorb or reflect neutrons. The reflection compensator 80, 80' can reflect neutrons reflected or scattered into the gap into the moderator 14 or the reflector 15, thereby increasing the yield of epithermal neutrons and reducing the time that the irradiated body needs to be irradiated. In another aspect, it avoids leakage of neutrons to the outside the beam shaping assembly 10 to cause adversely affect to the instruments of the neutron capture therapy system, and improves radiation safety. In this embodiment of the present disclosure, the content of lead in the lead alloy is greater than or equal to 85%, and the content of aluminum in the aluminum alloy is greater than or equal to 85%.

Simulated experiments are performed below to statistics and analyze the epithermal neutron fluxes, fast neutron fluxes, and epithermal neutron forwardness reference values and the intensity of γ rays in the related structures of the present disclosure. In all the simulated experiments of the present disclosure, the energy of the charged particle source is 2.5 MeV and 10 mA, the count surfaces of epithermal neutron fluxes and fast neutron fluxes are located at the beam exit 18 of the beam shaping assembly 10, the diameter of the beam exit 18 is 14 CM, and the count surface of the intensity of the γ ray is the left end surface of the beam shaping assembly 10.

Referring to FIG. 1 and FIG. 2, the target 31 in the first embodiment is accommodated in the moderator 14. Referring to FIG. 8, the target 31 in the fourth embodiment is disposed outside the moderator 14. To compare the impact of the arrangement positions of the target 31 in the first embodiment and the fourth embodiment on the epithermal neutron fluxes, the fast neutron fluxes, and the neutron forwardness, simulated experiments are performed to obtain the data in Table 1 for comparison and analysis. In the present disclosure, the thickness of the moderator 14 is the size of the moderator 14 in the direction of the neutron beam axis X1.

TABLE 1

Epithermal neutron fluxes, fast neutron fluxes, and epithermal neutron forwardness reference values when the target is accommodated in the moderator and is disposed outside of the moderator

| Model | Epithermal neutron forwardness reference value | Epithermal neutron flux (n/cm$^2$/sec) | Fast neutron flux (n/cm$^2$/sec) |
|---|---|---|---|
| The target is outside of the moderator. The thickness of the moderator is 25 cm. | 0.679 | 1.28E+09 | 1.38E+08 |
| The target is inside the moderator. The thickness of the moderator is 25 cm. | 0.682 | 1.26E+09 | 1.21E+08 |

It can be learned from Table 1 that compared with the target 31 set outside of the moderator 14, when the target 31 is accommodated in the moderator 14, the neutron forwardness does not change significantly, the intensity of fast neutrons is reduced by 12.52%, and the intensity of an epithermal neutron beam is only reduced by 1.83%. It can be learned that the arrangement manner of the target 31 is accommodated in the moderator 14 is better than the arrangement manner of the target 31 is disposed outside the moderator 14. It should be noted that the closer the epithermal neutron forwardness reference value is to 1, the better the epithermal neutron forwardness.

Referring to FIG. 1 and FIG. 2, in the first embodiment, the first moderating unit 140 is a three-step moderator. Referring to FIG. 9 to FIG. 12, in the fifth to the eighth embodiments, the first moderating unit assemblies 140 is set as a stepless moderator, a two-step moderator, a three-step moderator, a four-step moderator, and a ten-step moderator respectively. To compare the impact of the first moderating unit assemblies 140 with different quantities of steps on epithermal neutron fluxes, fast neutron fluxes, and neutron forwardness, in the present disclosure, on the premise of keeping the angle θ and the depth X of the target 31 entering the moderator 14, the first moderating unit 140 is set as a stepless moderator, a two-step moderator, a three-step moderator, a four-step moderator, and a ten-step moderator respectively. The simulated experiments are performed to obtain the data in Table 2 for comparison and analysis.

TABLE 2

Epithermal neutron fluxes, fast neutron fluxes, and epithermal neutron forwardness reference values when the first moderating unit is set as a stepless moderator, a one-step moderator, a two-step moderator, a three-step moderator, a four-step moderator, and a ten-step moderator respectively

| Model | Epithermal neutron forwardness reference value | Epithermal neutron flux (n/cm$^2$/sec) | Fast neutron flux (n/cm$^2$/sec) |
|---|---|---|---|
| Stepless moderator | 0.682 | 1.26E+09 | 1.21E+08 |
| Two-step moderator | 0.682 | 1.27E+09 | 1.22E+08 |
| Three-step moderator | 0.682 | 1.28E+09 | 1.22E+08 |
| Four-step moderator | 0.681 | 1.28E+09 | 1.23E+08 |
| Ten-step moderator | 0.682 | 1.28E+09 | 1.24E+08 |

It can be learned from the data in Table 2 that setting the first moderating unit 140 as a stepless (cylindrical moderator) or multi-step moderator has a little affect to the intensity of epithermal neutrons, the intensity of fast neutrons, and neutron forwardness. However, a smaller amount of moderator material is needed to manufacture a multi-step moderator than a stepless moderator. In consideration of both material costs and manufacturing process costs, preferably, the first moderating unit assembly 140 is set as a three-step or a four-step moderator.

Referring to FIG. 1 to FIG. 4, FIG. 8, and FIG. 10 to FIG. 12, a gap exists between the accommodating cavity 12 and the vacuum tube 30, and the reflection compensator 50 is filled in the gap. To compare the impact of filled or unfilled the reflection compensator 50 in the gap on the intensity of epithermal neutrons, the intensity of fast neutrons, and epithermal neutron forwardness, Table 3 is provided for detailed comparison and analysis.

conical moderator, the intensity of epithermal neutrons can be increased in different degrees by filling the reflection compensator 50 in the gap between the accommodating cavity 12 and the vacuum tube 30, and the neutron forwardness is not significantly affected.

Referring to FIG. 1, FIG. 2, and FIG. 8 to FIG. 12, the shielding assembly 40 is arranged at a left end of the beam shaping assembly 10 in the present disclosure, that is, a charged particle beam entrance end, to prevent the neutron beam and the γ ray formed at the target 31 from overflowing from the left end surface of the beam shaping assembly 10. The following list the data of the intensity of neutrons and the intensity of the γ ray at the left end of the beam shaping assembly 10 and the intensity of epithermal neutrons, the intensity of fast neutrons, and epithermal neutron forwardness reference values at the beam exit 18 of the beam

TABLE 3

Epithermal neutron fluxes, fast neutron fluxes, and epithermal neutron forwardness reference values when the reflection compensator is filled and unfilled

| | Model | Epithermal neutron forwardness reference value | Epithermal neutron flux (n/cm²/sec) | Increase ratio | Fast neutron flux (n/cm²/sec) | Increase ratio |
|---|---|---|---|---|---|---|
| Two-step | Without reflection compensation | 0.682 | 1.27E+09 | | 1.22E+08 | |
| | With reflection compensation | 0.683 | 1.36E+09 | 7.37% | 1.26E+08 | 3.72% |
| Three-step | Without reflection compensation | 0.682 | 1.28E+09 | | 1.22E+08 | |
| | With reflection compensation | 0.683 | 1.37E+09 | 7.33% | 1.27E+08 | 3.68% |
| Four-step | Without reflection compensation | 0.681 | 1.28E+09 | | 1.23E+08 | |
| | With reflection compensation | 0.683 | 1.37E+09 | 735% | 1.27E+08 | 3.56% |
| Ten-step | Without reflection compensation | 0.682 | 1.28E+09 | | 1.24E+08 | |
| | With reflection compensation | 0.683 | 1.38E+09 | 7.46% | 1.28E+08 | 3.40% |

It can be learned from Table 3 that compared with the reflection compensator 50 is not filled in the gap between the accommodating cavity 12 and the vacuum tube 30, when the reflection compensator 50 is filled in the gap between the accommodating cavity 12 and the vacuum tube 30, the intensity of an epithermal neutron beam is increased by 7.33% to 7.46%, the neutron forwardness is significantly change.

The present disclosure only lists the data obtained through simulated experiments of the moderator 140 is set as a multi-step moderator. However, research indicates that when the moderator 14 is set as the entire cylindrical moderator shown in FIG. 9 or is set as the double-conical moderator shown in FIG. 4 or is set as a moderator that includes one conical moderator and one cylindrical moderator or is set as a moderator that includes a multi-step moderator and one shaping assembly 10 when the first moderating unit assemblies 140 is set as a stepless moderator, a two-step moderator, a three-step moderator, a four-step moderator, and a ten-step moderator respectively and when the shielding assembly 40 and/or the reflection compensator 50 is disposed or the shielding assembly 40 and/or the reflection compensator 50 is not disposed, to analyze the impact of the shielding assembly 40 and the reflection compensator 50 on the intensity of neutrons and the intensity of the γ ray at the left end of the beam shaping assembly 10 and the intensity of epithermal neutrons, the intensity of fast neutrons, and epithermal neutron forwardness at the beam exit 18 of the beam shaping assembly 10. The same unit "n/cm²/sec" is used for the intensity of neutrons, the γ ray, epithermal neutrons, and fast neutrons.

TABLE 4

The intensity of neutrons and the intensity of the γ ray at the left end of the beam shaping assembly and the intensity of epithermal neutrons, the intensity of fast neutrons, and epithermal neutron forwardness reference values at the beam exit of the beam shaping assembly

| Model | | | Left end of a beam shaping assembly | | | | Beam exit | | | |
|---|---|---|---|---|---|---|---|---|---|---|
| | Shielding assembly | Reflection compensator | Neutron | Ratio | γ ray | Ratio | Epithermal neutron forwardness reference value | Epithermal neutron | Fast neutron | Epithermal neutron/Fast neutron |
| Stepless | No | No | 2.45E+08 | 100.00% | 6.63E+06 | 100.00% | 0.684 | 1.26E+09 | 1.21E+08 | 10.46 |
| | No | Yes | 2.22E+08 | 90.68% | 5.26E+06 | 79.27% | 0.684 | 1.36E+09 | 1.25E+08 | 10.81 |
| | Yes | No | 9.67E+07 | 39.43% | 3.61E+06 | 54.38% | 0.684 | 1.31E+09 | 1.22E+08 | 10.76 |
| | Yes | Yes | 9.31E+07 | 37.95% | 3.45E+06 | 52.01% | 0.684 | 1.38E+09 | 1.26E+08 | 11.00 |
| Two-step | No | No | 2.46E+08 | 100.00% | 6.43E+06 | 100.00% | 0.684 | 1.28E+09 | 1.22E+08 | 10.48 |
| | No | Yes | 2.23E+08 | 90.71% | 5.11E+06 | 79.44% | 0.683 | 1.37E+09 | 1.26E+08 | 10.84 |
| | Yes | No | 9.76E+07 | 39.69% | 3.54E+06 | 55.08% | 0.683 | 1.33E+09 | 1.23E+08 | 10.78 |
| | Yes | Yes | 9.40E+07 | 38.19% | 3.40E+06 | 52.81% | 0.683 | 1.40E+09 | 1.27E+08 | 11.02 |
| Three-step | No | No | 2.46E+08 | 100.00% | 6.36E+06 | 100.00% | 0.683 | 1.28E+09 | 1.23E+08 | 10.46 |
| | No | Yes | 2.23E+08 | 90.70% | 5.06E+06 | 79.55% | 0.683 | 1.37E+09 | 1.27E+08 | 10.82 |
| | Yes | No | 9.81E+07 | 39.83% | 3.51E+06 | 55.21% | 0.682 | 1.33E+09 | 1.24E+08 | 10.76 |
| | Yes | Yes | 9.44E+07 | 38.31% | 3.37E+06 | 53.00% | 0.682 | 1.40E+09 | 1.28E+08 | 11.00 |
| Four-step | No | No | 2.47E+08 | 100.00% | 6.31E+06 | 100.00% | 0.682 | 1.29E+09 | 1.23E+08 | 10.47 |
| | No | Yes | 2.24E+08 | 90.73% | 5.02E+06 | 79.65% | 0.682 | 1.38E+09 | 1.27E+08 | 10.84 |
| | Yes | No | 9.84E+07 | 39.90% | 3.50E+06 | 55.46% | 0.682 | 1.33E+09 | 1.24E+08 | 10.77 |
| | Yes | Yes | 9.46E+07 | 38.38% | 3.36E+06 | 53.26% | 0.683 | 1.41E+09 | 1.2SE+08 | 11.02 |
| Ten-step | No | No | 2.47E+08 | 100.00% | 6.23E+06 | 100.00% | 0.683 | 1.29E+09 | 1.24E+08 | 10.40 |
| | No | Yes | 2.24E+08 | 90.74% | 4.96E+06 | 79.68% | 0.683 | 1.38E+09 | 1.2SE+08 | 10.79 |
| | Yes | No | 9.89E+07 | 40.05% | 3.47E+06 | 55.80% | 0.682 | 1.34E+09 | 1.25E+08 | 10.71 |
| | Yes | Yes | 9.51E+07 | 38.52% | 3.34E+06 | 53.62% | 0.682 | 1.41E+09 | 1.29E+08 | 10.98 |

It can be learned from Table 4 that adding the shielding assembly 40 can significantly reduce the intensity of the γ ray and the intensity of the neutron beam behind the beam shaping assembly 10, the shielding assembly 40 does not significantly affect the intensity of epithermal neutrons and the intensity of fast neutrons at the beam exit 18, and adding the reflection compensator 50 can significantly increase the intensity of epithermal neutrons at the beam exit 18.

The present disclosure only lists the data obtained through simulated experiments of the moderator 140 is set as a stepless moderator or multi-step moderator. However, research indicates that when the moderator 14 is set as the double-conical moderator shown in FIG. 4 or is set as a moderator that includes one conical moderator and one cylindrical moderator or is set as a moderator that includes a multi-step moderator and a conical moderator, the intensity of epithermal neutrons can be increased in different degrees, the intensity of the γ ray and the intensity of the neutron beam behind the beam shaping assembly 10 can be reduced in different degrees, and the neutron forwardness is not significantly affected by filling the reflection compensator 50 in the gap between the accommodating cavity 12 and the vacuum tube 30 and by disposing the shielding assembly 40 at the left end of the beam shaping assembly 10.

In the following, the effect of changing the depth X of the target 31 entering into the moderator 14, that is, changing the size of the first moderating unit 140 in the direction of the neutron beam axis X1, on epithermal neutron fluxes, fast neutron fluxes, and neutron forwardness is analyzed through simulated experiment date under the premised of keeping the angle θ unchanged.

TABLE 5

Epithermal neutron fluxes, fast neutron fluxes, and neutron forwardness reference values when the depth X of the target entering into the moderator are respectively 5 CM, 10 CM, 15 CM, and 20 CM

| Model | | Epithermal neutron forwardness reference value | Epithermal neutron flux (n/cm²/sec) | Ratio | Fast neutron flux (n/cm²/sec) | Ratio | Epithermal neutron/Fast neutron |
|---|---|---|---|---|---|---|---|
| Stepless | X = 5 cm | 0.681 | 1.27E+09 | 100.00% | 1.25E+08 | 100.00% | 10.16 |
| | X = 10 cm | 0.682 | 1.26E+09 | 99.21% | 1.21E+08 | 96.80% | 10.43 |
| | X = 15 cm | 0.683 | 1.25E+09 | 98.43% | 1.19E+08 | 95.20% | 10.46 |
| | X = 20 cm | 0.682 | 1.24E+09 | 97.64% | 1.19E+08 | 95.20% | 10.45 |
| Two-step | X = 5 cm | 0.681 | 1.28E+09 | 100.00% | 1.26E+08 | 100.00% | 10.10 |
| | X = 10 cm | 0.682 | 1.27E+09 | 99.22% | 1.22E+08 | 96.83% | 10.44 |
| | X = 15 cm | 0.682 | 1.26E+09 | 98.44% | 1.20E+08 | 95.24% | 10.54 |
| | X = 20 cm | 0.682 | 1.25E+09 | 97.66% | 1.19E+08 | 94.44% | 10.54 |
| Three-step | X = 5 cm | 0.681 | 1.28E+09 | 100.00% | 1.27E+08 | 100.00% | 10.04 |
| | X = 10 cm | 0.682 | 1.28E+09 | 100.00% | 1.22E+08 | 96.06% | 10.42 |
| | X = 15 cm | 0.682 | 1.27E+09 | 99.22% | 1.20E+08 | 94.49% | 10.55 |
| | X = 20 cm | 0.683 | 1.26E+09 | 98.44% | 1.19E+08 | 93.70% | 10.56 |
| Four-step | X = 5 cm | 0.681 | 1.28E+09 | 100.00% | 1.27E+08 | 100.00% | 10.05 |
| | X = 10 cm | 0.681 | 1.28E+09 | 100.00% | 1.23E+08 | 96.85% | 10.43 |
| | X = 15 cm | 0.682 | 1.27E+09 | 99.22% | 1.20E+08 | 94.49% | 10.59 |
| | X = 20 cm | 0.682 | 1.26E+09 | 98.44% | 1.19E+08 | 93.70% | 10.56 |

TABLE 5-continued

Epithermal neutron fluxes, fast neutron fluxes, and neutron forwardness reference values when the depth X of the target entering into the moderator are respectively 5 CM, 10 CM, 15 CM, and 20 CM

| Model | | Epithermal neutron forwardness reference value | Epithermal neutron flux (n/cm$^2$/sec) | Ratio | Fast neutron flux (n/cm$^2$/sec) | Ratio | Epithermal neutron/Fast neutron |
|---|---|---|---|---|---|---|---|
| Ten-step | X = 5 cm | 0.681 | 1.28E+09 | 100.00% | 1.28E+08 | 100.00% | 10.00 |
| | X = 10 cm | 0.682 | 1.28E+09 | 100.00% | 1.24E+08 | 96.88% | 10.36 |
| | X = 15 cm | 0.682 | 1.28E+09 | 100.00% | 1.21E+08 | 94.53% | 10.55 |
| | X = 20 cm | 0.682 | 1.27E+09 | 99.22% | 1.20E+08 | 93.75% | 10.57 |

It can be learned from Table 5 that as the depth of the target 31 extending into the moderator 14 increases, the intensity of the epithermal neutron beam slightly decreases (about 2%), the intensity of fast neutrons decreases by about 6%, the epithermal neutron forwardness shows no significant change, and the ratio of the epithermal neutron flux to the fast neutron flux is increased.

The present disclosure only lists the data obtained through simulated experiments of the moderator 140 is set as a stepless moderator or a multi-step moderator. However, research indicates that when the moderator 14 is set as the double-conical moderator shown in FIG. 4 or is set as a moderator that includes one conical moderator and one cylindrical moderator or is set as a moderator that includes a multi-step moderator and a conical moderator, as the depth of the target 3 extending into the moderator 14 increases, the intensity of the epithermal neutron beam slightly decreases, the intensity of fast neutrons decreases, the epithermal neutron forwardness shows no significant change, and the ratio of the epithermal neutron flux to the fast neutron flux is increased.

To compare the impact on yield of epithermal neutrons, a contamination amount of fast neutrons, and an irradiation time when the reflection compensator 80 are respectively a lead alloy and an aluminum alloy and there is no reflection compensator 80 (that is, air is filled) in the gaps between the cooling devices 20, 20' and the accommodating pipes 13, 13', Table 6 to Table 8 are listed for detailed comparison.

Table 6 shows the yield of epithermal neutrons (n/cm$^2$ mA) when filling air, aluminum alloy, and lead alloy respectively under different accommodating cavity hole diameters:

TABLE 6

Yield of epithermal neutrons (n/cm$^2$mA)

| | Accommodating cavity hole diameter (CM) | | | | | |
|---|---|---|---|---|---|---|
| | 16 CM | 18 CM | 20 CM | 22 CM | 24 CM | 26 CM |
| Air | 8.20E+07 | 7.82E+07 | 7.38E+07 | 6.97E+07 | 6.56E+07 | 6.22E+07 |
| Aluminum alloy | 8.74E+07 | 8.58E+07 | 8.40E+07 | 8.23E+07 | 8.07E+07 | 7.88E+07 |
| Lead alloy | 8.94E+07 | 8.88E+07 | 8.79E+07 | 8.69E+07 | 8.63E+07 | 8.53E+07 |

Table 7 shows contamination amounts of fast neutrons (Gy-cm$^2$/n) when filling air, aluminum alloy, and lead alloy respectively under different accommodating cavity hole diameters:

TABLE 7

Contamination amount of fast neutrons (Gy-cm$^2$/n)

| | Accommodating cavity hole diameter (CM) | | | | | |
|---|---|---|---|---|---|---|
| | 16 CM | 18 CM | 20 CM | 22 CM | 24 CM | 26 CM |
| Air | 7.01E−13 | 7.51E−13 | 8.23E−13 | 8.95E−13 | 9.80E−13 | 1.06E−12 |
| Aluminum alloy | 6.54E−13 | 6.83E−13 | 7.17E−13 | 7.54E−13 | 7.90E−13 | 8.37E−13 |
| Lead alloy | 6.56E−13 | 6.83E−13 | 7.18E−13 | 7.52E−13 | 7.87E−13 | 8.29E−13 |

Table 8 shows an irradiation time (minute) that an irradiated body requires when filling air, aluminum alloy, and lead alloy respectively under different accommodating cavity hole diameters:

TABLE 8

| | Irradiation time (Min) that an irradiated body requires | | | | | |
|---|---|---|---|---|---|---|
| | Accommodating cavity hole diameter (CM) | | | | | |
| | 16 CM | 18 CM | 20 CM | 22 CM | 24 CM | 26 CM |
| Air | 30.86 | 31.16 | 32.29 | 32.66 | 33.42 | 34.12 |
| Aluminum alloy | 29.65 | 29.07 | 30.46 | 29.42 | 29.22 | 29.39 |
| Lead alloy | 28.94 | 28.00 | 28.37 | 27.76 | 27.91 | 28.04 |

It can be learned from Table 6 to Table 8 that when the accommodating cavity hole diameter is the same, compared with air filling, the yield of epithermal neutrons is higher when filled with lead alloy or aluminum alloy, and the contamination amount of fast neutrons and the required irradiation time is less.

The neutron capture therapy system disclosed in the present disclosure is not limited to the content in the foregoing embodiments and the structures represented in the accompanying drawings. For example, the moderator may be disposed to be a cone or a polygonal prism, several cooling devices may be disposed, and several accommodating pipes are correspondingly provided. All obvious changes, replacements or modifications made to the materials, shapes, and positions of the members based on the present disclosure fall within the protection scope of the present disclosure.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A neutron capture therapy system, comprising:
   a beam shaping assembly and a vacuum tube disposed in the beam shaping assembly, wherein the beam shaping assembly comprises:
   a beam entrance,
   an accommodating cavity for accommodating the vacuum tube,
   a moderator adjacent to an end of the accommodating cavity, wherein the moderator moderates neutrons generated from a target to an epithermal neutron energy range,
   a reflector surrounding the moderator, wherein the reflector guides deflecting neutrons back to the moderator to enhance an intensity of an epithermal neutron beam,
   a radiation shield disposed in the beam shaping assembly, wherein the radiation shield is configured to shield against leaked neutrons and photons to reduce a dose to a normal tissue in a non-irradiation area, and
   a beam exit, wherein the target is disposed at an end of the vacuum tube, the target undergoes a nuclear reaction with a charged particle beam entering through the beam entrance to generate neutrons, the neutrons form a neutron beam, and the neutron beam is emitted from the beam exit and defines a neutron beam axis, and
   wherein the moderator at least comprises two cylindrical moderating members with different outer diameters respectively, the moderator has a first end close to the beam entrance and a second end close to the beam exit, and the target is accommodated between the first end and the second end.

2. The neutron capture therapy system according to claim 1, wherein the moderator comprises a first moderating unit close to the beam entrance and a second moderating unit closely attached to the first moderating unit and close to the beam exit, the first moderating unit at least comprises two cylindrical moderating members with different outer diameters respectively, wherein all of the beam entrance, the moderator and the beam exit are extended along the neutron beam axis, and wherein a distance from the target to the beam exit is less than a distance from the first end to the beam exit.

3. The neutron capture therapy system according to claim 2, wherein the first moderating unit comprises three cylindrical moderating members with different outer diameters respectively, the first moderating unit comprises a first moderating portion close to the beam entrance, a second moderating portion closely attached to the first moderating portion, and a third moderating portion closely attached to the second moderating portion, the first moderating portion, the second moderating portion and the third moderating portion are sequentially arranged along an axial direction of the neutron beam, the first moderating portion defines a first outer diameter, the second moderating portion defines a second outer diameter greater than the first outer diameter, the third moderating portion defines a third outer diameter greater than the second outer diameter, the second moderating unit defines a fourth outer diameter equal to the third outer diameter.

4. The neutron capture therapy system according to claim 3, wherein the first moderating portion comprises a first front end surface close to the beam entrance, a first rear end surface close to the beam exit and a first outer circumferential surface, the second moderating portion comprises a second front end surface closely attached to the first rear end surface, a second rear end surface close to the beam exit and a second outer circumferential surface, the third moderating portion comprises a third front end surface closely attached to the second rear end surface, a third rear end surface close to the beam exit and a third outer circumferential surface, the second moderating unit comprises a fourth front end surface closely attached to the third rear end surface, a fourth rear end surface close to the beam exit and a fourth outer circumferential surface, in the tangent surface passing through the neutron beam axis, the first front end surface intersects the first outer circumferential surface to obtain a first intersection point, the second front end surface intersects the second outer circumferential surface to obtain a second intersection point, the third front end surface intersects the third outer circumferential surface to obtain a third intersection point, and the first intersection point, the second intersection point and the third intersection point are located on a same straight line or one arc lin.

5. The neutron capture therapy system according to claim 2, wherein a cross section of the second moderating unit is conical or cylindrical or steped-shaped.

6. The neutron capture therapy system according to claim 2, wherein a depth of the target entering into the moderator is less than or equal to a length of the first moderating unit in an axial direction of the neutron beam.

7. The neutron capture therapy system according to claim 1, wherein a reflection compensator is filled between the accommodating cavity and the vacuum tube, and the reflection compensator is lead or Al or C.

8. The neutron capture therapy system according to claim 1, wherein the first end protrudes from the target along the neutron beam axis in a direction towards the beam entrance, and the second end protrudes from the target along the neutron beam axis in a direction towards the beam exit.

9. The neutron capture therapy system according to claim 1, wherein the reflector protrudes from the moderator on both sides of the neutron beam axis, the accommodating cavity comprises a reflector accommodating cavity surrounded by the reflector and a moderator accommodating cavity extending from the reflector accommodating cavity and surrounded by the moderator, the vacuum tube comprises an extending section accommodated in the reflector accommodating cavity and an insertion section extending from the extending section and accommodated in the moderator accommodating cavity, and the target is disposed at an end of the insertion section.

10. The neutron capture therapy system according to claim 1, wherein the neutron capture therapy system further comprises at least one cooling device, at least one accommodating pipe disposed in the beam shaping assembly for accommodating the cooling device and a lead alloy or an aluminum alloy filled between the cooling device and an inner wall of the accommodating pipe.

11. The neutron capture therapy system according to claim 1, wherein the neutron capture therapy system further comprises a shielding assembly disposed at the beam entrance and closely attached to the beam shaping assembly.

12. The neutron capture therapy system according to claim 10, wherein the cooling device comprises a first cooling portion arranged in a vertical direction and located in front of the target for cooling the target and a second cooling portion and a third cooling portion extending in an axial direction of the neutron beam and respectively located on two sides of the vacuum tube, the first cooling portion is connected between the second cooling portion and the third cooling portion, the second cooling portion inputs a cooling medium into the first cooling portion, and the third cooling portion outputs the cooling medium in the first cooling portion.

13. A neutron capture therapy system, comprising:
a beam shaping assembly,
a vacuum tube disposed in the beam shaping assembly, and
a target disposed at an end of the vacuum tube, wherein the target undergoes a nuclear reactions with a charged particle beam entering through the beam entrance to generate neutrons,
wherein the beam shaping assembly comprises:
a beam entrance,
an accommodating cavity for accommodating the vacuum tube,
a moderator adjacent to an end of the accommodating cavity, wherein the moderator at least comprises two hollow cylindrical moderating members with different outer diameters and same inner diameter respectively,
a reflector surrounding the moderator, and
a beam exit.

14. The neutron capture therapy system according to claim 13, wherein a reflection compensator is filled between the accommodating cavity and the vacuum tube, and the reflection compensator is lead or Al or C.

15. The neutron capture therapy system according to claim 13, wherein the neutron capture therapy system further comprises at least one cooling device, at least one accommodating pipe disposed in the beam shaping assembly for accommodating the cooling device, and a lead alloy or an aluminum alloy is filled between the cooling device and an inner wall of the accommodating pipe.

16. The neutron capture therapy system according to claim 13, wherein the moderator comprises a first end close to the beam entrance and a second end close to the beam exit, and the target is accommodated between the first end and the second end.

17. A neutron capture therapy system, comprising:
a beam shaping assembly, the beam shaping assembly comprises:
a beam entrance,
a moderator,
a reflector surrounding the moderator, and
a beam exit,
wherein the moderator at least comprises two hollow cylindrical moderating members with different outer diameters respectively.

18. The neutron capture therapy system according to claim 17, wherein the moderator comprises a first moderating unit close to the beam entrance and a second moderating unit closely attached to the first moderating unit and close to the beam exit, the first moderating unit at least comprises two hollow cylindrical moderating members with different outer diameters respectively.

19. The neutron capture therapy system according to claim 17, wherein the neutron capture therapy system further comprises at least one cooling device, at least one accommodating pipe disposed in the beam shaping assembly for accommodating the cooling device and a lead alloy or an aluminum alloy filled between the cooling device and an inner wall of the accommodating pipe.

20. The neutron capture therapy system according to claim 17, wherein the neutron capture therapy system further comprises a vacuum tube disposed in the beam shaping assembly, the beam shaping assembly further comprises an accommodating cavity for accommodating the vacuum tube, a reflection compensator is filled between the accommodating cavity and the vacuum tube, and the reflection compensator is lead or Al or C.

* * * * *